US005534500A

United States Patent [19]

Casamassina et al.

[11] Patent Number: 5,534,500

[45] Date of Patent: Jul. 9, 1996

[54] PROCESS FOR PREPARING SURFACTANT MIXTURES HAVING HIGH SOLIDS CONTENT

[75] Inventors: Thomas Casamassina, Totowa; Florencio Morales, Jr., Jersey City; Barry A. Salka, Fair Lawn, all of N.J.; John Fallon, Point Pleasant, Pa.; Sureshchandra G. Desai, Wayne, N.J.; Patrick M. McCurry, Jr., Lansdale, Pa.

[73] Assignee: Henkel Corporation, Plymouth Meeting, Pa.

[21] Appl. No.: 293,861

[22] Filed: Aug. 22, 1994

Related U.S. Application Data

[63] Continuation-in-part of Ser. No. 120,624, Sep. 13, 1993.

[51] Int. Cl.$^6$ .............................. A61K 31/70; C07G 3/00; C07H 1/00; C11D 9/00

[52] U.S. Cl. .......................... 252/353; 536/4.1; 536/18.5; 536/124; 252/357; 252/356; 510/537; 514/25

[58] Field of Search .......................... 536/124, 4.1, 18.5; 514/25; 252/108, 367, 368, DIG. 1

[56] References Cited

U.S. PATENT DOCUMENTS

| | | | |
|---|---|---|---|
| 4,406,833 | 9/1983 | Boehme et al. | 260/123.7 |
| 4,483,787 | 11/1984 | Jones et al. | 530/356 |
| 4,857,213 | 8/1989 | Caswell et al. | 252/8.75 |
| 5,073,292 | 12/1991 | Hessel et al. | 252/174.12 |
| 5,174,927 | 12/1992 | Honsa | 252/543 |
| 5,227,086 | 7/1993 | Kacher | 252/112 |
| 5,242,615 | 9/1993 | Urfer et al. | 252/174.17 |
| 5,258,142 | 11/1993 | Giesen et al. | 252/552 |
| 5,266,690 | 11/1993 | McCurry, Jr. et al. | 536/18.6 |
| 5,308,526 | 5/1994 | Dias et al. | 252/125 |

*Primary Examiner*—Douglas W. Robinson
*Assistant Examiner*—Everett White
*Attorney, Agent, or Firm*—Wayne C. Jaeschke; John E. Drach; Henry E. Millson, Jr.

[57] ABSTRACT

Highly concentrated mixtures of surfactants are obtained by a method which comprises adding the acid form of a neutralizable surfactant to an aqueous composition comprised of a base and an alkyl polyglycoside.

27 Claims, No Drawings

PROCESS FOR PREPARING SURFACTANT MIXTURES HAVING HIGH SOLIDS CONTENT

CROSS-REFERENCE TO RELATED APPLICATIONS

This application is a continuation-in-part of application Ser. No. 08/120,624, filed Sep. 13, 1993, the entire contents of which are incoporated herein by reference.

BACKGROUND OF THE INVENTION

1. Field of the Invention

This invention relates to a process for making surfactant mixtures having a relatively high solids content.

2. Description of the Related Art

Surfactant manufacturers normally seek to prepare their products having as great a solids concentration as possible in order to minimize transportation costs. However, it not always possible to take advantage of such economic benefits when mixtures containing the sodium salts of certain surfactants are being shipped because of the difficulty in preparing such mixtures in highly concentrated form. For example, surfactant mixtures comprised of 25% by weight of the sodium salt of an alcohol sulfate and 25% by weight of an alkyl polyglycoside cannot be made by the conventional method of mixing aqueous solutions of the two components because the water solubility of an alcohol sulfate in water is about 30% by weight while the maximum solubility of a fatty alkyl polyglycoside in water can be up to about 65% by weight. Therefore, it would be impossible to make a surfactant mixture containing an alkyl polyglycoside and having 30% by weight of, for example, sodium lauryl sulfate by simply mixing a 30% aqueous sodium lauryl sulfate solution and an aqueous alkyl polyglycoside solution. Such solubility limitations are not encountered with the corresponding ammonium salts of neutralizable surfactants. Therefore, mixtures containing high concentrations of such ammonium salts are obtainable by mixing highly concentrated solutions. In order to minimize the costs of shipping a highly concentrated surfactant mixture, such as one containing sodium lauryl sulfate and an alkyl polyglycoside, a manufacturer would strive to make a surfactant mixture having as little water as possible. The present invention is a method for making a relatively highly concentrated surfactant mixture containing an anionic surfactant and an alkyl polyglycoside regardless of whether or not the anionic surfactant is available itself in a highly concentrated form. The process according to the invention is particularly useful for preparing relatively highly concentrated surfactant mixtures containing the sodium salts of moderately soluble anionic surfactants and alkyl polyglycosides.

SUMMARY OF THE INVENTION

The surprising discovery has been made that highly concentrated mixtures of surfactants can be obtained by a method which comprises adding the acid form of a neutralizable surfactant to an aqueous composition comprised of a base and an alkyl polyglycoside. The concentration of the base in the aqueous composition is such that the pH of the final surfactant mixture has a value of from about 6 to about 8. The method according to the invention affords surfactant mixtures having a total surfactant concentration which cannot be achieved by mixing surfactants in their conventional, commercially available concentrations.

DESCRIPTION OF THE PREFERRED EMBODIMENTS

Other than in the operating examples, or where otherwise indicated, all numbers expressing quantities of ingredients or reaction conditions used herein are to be understood as modified in all instances by the term "about".

The alkyl polyglycosides which can be used in the process according to the invention have the formula I $$R_1O(Z)_a \qquad \text{I}$$

wherein $R_1$ is a monovalent organic radical having from about 6 to about 30 carbon atoms; Z is saccharide residue having 5 or 6 carbon atoms; a is a number having a value from 1 to about 6 and represents the average degree of polymerization of the saccharide residue. The alkyl polyglycosides which can be used in the compositions according to the invention have the formula I and are commercially available, for example, as APG®, GLUCOPON®, or PLANTAREN® surfactants from Henkel Corporation, Ambler, Pa., 19002. Examples of such surfactants include but are not limited to:

1. APG® 225 Surfactant—an alkylpolyglycoside in which the alkyl group contains 8 to 10 carbon atoms and having an average degree of polymerization of 1.7.
2. APG® 425 Surfactant—an alkyl polyglycoside in which the alkyl group contains 8 to 16 carbon atoms and having an average degree of polymerization of 1.6.
3. APG® 625 Surfactant—an alkyl polyglycoside in which the alkyl groups contains 12 to 16 carbon atoms and having an average degree of polymerization of 1.6.
4. APG® 325 Surfactant—an alkyl polyglycoside in which the alkyl groups contains 9 to 11 carbon atoms and having an average degree of polymerization of 1.6.
5. GLUCOPON® 600 Surfactant—an alkyl polyglycoside in which the alkyl groups contains 12 to 16 carbon atoms and having an average degree of polymerization of 1.4.
6. PLANTAREN® 2000 Surfactant—a $C_{8-16}$ alkyl polyglycoside in which the alkyl group contains 8 to 16 carbon atoms and having an average degree of polymerization of 1.4.
7. PLANTAREN® 1300 Surfactant—a $C_{12-16}$ alkyl polyglycoside in which the alkyl groups contains 12 to 16 carbon atoms and having an average degree of polymerization of 1.6.

Other examples include alkyl polyglycoside surfactant compositions which are comprised of mixtures of compounds of formula I wherein Z represents a moiety derived from a reducing saccharide containing 5 or 6 carbon atoms; a is zero; and $R_1$ is an alkyl radical having from 8 to 20 carbon atoms. The compositions are characterized in that they have increased surfactant properties and an HLB in the range of about 10 to about 16 and a non-Flory distribution of glycosides, which is comprised of a mixture of an alkyl monoglycoside and a mixture of alkyl polyglycosides having varying degrees of polymerization of 2 and higher in progressively decreasing amounts, in which the amount by weight of polyglycoside having a degree of polymerization of 2, or mixtures thereof with the polyglycoside having a degree of polymerization of 3, predominate in relation to the amount of monoglycoside, said composition having an average degree of polymerization of about 1.8 to about 3. Such compositions, also known as peaked alkyl polyglucosides, can be prepared by separation of the monoglycoside from the original reaction mixture of alkyl monoglycoside and alkyl polyglycosides after removal of the alcohol. This separation may be carried out by molecular distillation and normally results in the removal of about 70–95% by weight of the alkyl monoglycosides. After removal of the alkyl monoglycosides, the relative distribution of the various components, mono- and poly-glycosides, in the resulting product changes and the concentration in the product of the polyglycosides relative to the monoglycoside increases as well as the concentration of individual polyglycosides to the total, i.e. DP2 and DP3 fractions in relation to the sum of all DP fractions. Such compositions are disclosed in U.S. Pat. No. 5,266,690, the entire contents of which are incorporated herein by reference.

The neutralizable surfactants which can be used in the process according to the invention can be any surfactant which can exist in an acid form and subsequently converted to the anionic form through neutralization with a base. Examples of such surfactants include, but are not limited to, the acid form of alkyl aryl sulfonates such as linear alkyl benzene sulfonate, alkyl sulfonates, alkyl isethionates such as sodium cocoyl isethionate, alkyl sarcosonates, sulfosuccinates, alkyl ether sulfates such a sodium laureth-1 sulfate, alkyl sulfates such as sodium lauryl sulfate, alkyl taurates, and olefin sulfonates. Preferred surfactants are sodium lauryl sulfate, linear alkyl benzene sulfonate, sodium lauryl sulfate and sodium cocoyl isethionate.

Another type of neutralizable surfactant is a protein condensate which is the reaction product of a hydrolyzed protein and a fatty acid chloride. An example of a hydrolyzed protein is a hydrolyzed collagen which is commercially available as, for example, NUTRILAN® I or NUTRILAN® L, each of which is a trademark product of Henkel Corporation, Ambler, Pa. An example of a preferred protein condensate is the reaction product of a hydrolyzed collagen having a molecular weight of 500 Daltons and coco fatty acid chloride.

The base which can be used in the process according to the invention is any water soluble base which is deemed suitable for the neutralization of the acid form of the neutralizable surfactant. Such bases include alkali metal hydroxides such as sodium and potassium hydroxide used either in the solid form or as an aqueous solution such as a 50% aqueous solution of sodium hydroxide which is a preferred form of sodium hydroxide. The base can also be a water soluble amine such as ammonia or a water soluble primary, secondary, or tertiary amine or a water soluble polyamine such as ethylene diamine or diethylenetriamine. When the process according to the invention is used to prepare the sodium salt of a moderately soluble anionic surfactant such as sodium lauryl sulfate, the base will obviously be sodium hydroxide. Sodium hydroxide is an especially preferred base because of its presence in, and compatibility with, commercial alkyl polyglycosides and because the process according to the invention is particularly useful for preparing relatively highly concentrated surfactant mixtures containing the sodium salts of moderately soluble anionic surfactants and alkyl polyglycosides which are not otherwise obtainable by mixing solutions of the individual surfactants. Since commercially available alkyl polyglycosides may have a pH of greater than 10, the aqueous composition to which the acid form of the neutralizable surfactant is added may already contain sufficient base to neutralize the added acid form of the neutralizable surfactant and to ensure that the pH of the resulting surfactant mixture is from about 6 to about 8. Such a situation will typically be encountered when the number of equivalents of the acid form of the neutralizable surfactant is sufficiently less than the number of equivalents of base already present in the alkyl polyglycoside.

When the process according to the invention is used to prepare a surfactant mixture containing the ammonium salt of an anionic surfactant such as ammonium laureth-1 sulfate and an alkyl polyglycoside, the preferred base is aqueous ammonium hydroxide.

Other materials which may be used in the process according to the invention include polyethylene oxide which can be added to remove haze from the final product made by the process according to the invention. Polyethylene oxide polymers having a molecular weight in the range of from 200 to 1,000 are preferred and are commercially available, for example, from Union Carbide Corp. as CARBOWAX® polymers such as CARBOWAX® 700. Preferably, 1–3% by weight polyethylene oxide is added to the clarify the neutralization mix.

The process according to the invention may be carried out in a batch or continuous manner and in any type of vessel. The acid form of the neutralizable surfactant is added to an aqueous composition which is comprised of a base and an alkyl polyglycoside while the neutralization mixture is vigorously agitated to avoid lump formation. The amount of the base added to the aqueous composition is such that the pH of the final surfactant mixture has a value of from about 6 to about 8.

The process according to the invention results in compositions comprised of: (a) water, (b) from about 20% to about 40% by weight of the sodium salt an anionic surfactant selected from the group consisting of: (i) an alkyl isethionate, (ii) an alkyl sarcosinate, (iii) a sulfosuccinate, (iv) an alkyl sulfate, (v) an alkyl taurate, (vi) an olefin sulfonate, (vii) alkyl aryl sulfonate, (viii) an alkyl ether sulfate (ix), or a mixture comprised of any two or more of surfactants (i)–(ix) and, (c) from about 25% to about 50% by weight of an alkyl polyglycoside of the formula I as defined above.

One preferred composition is comprised of (a) water, (b) from about 20% to about 40% by weight of sodium lauryl sulfate and, (c) from about 25% to about 50% by weight of a $C_{8-16}$ alkyl polyglycoside. Another preferred composition is comprised of (a) water, (b) from about 20% to about 40% by weight of sodium lauryl sulfate and, (c) from about 25% to about 50% by weight of a mixture comprising a $C_{8-16}$ alkyl polyglycoside and a $C_{12-16}$ alkyl polyglycoside. Another preferred composition is comprised of (a) water, (b) from about 20% to about 40% by weight of sodium laureth-1 sulfate and, (c) from about 25% to about 50% by weight of a $C_{8-16}$ alkyl polyglycoside. Another preferred composition is comprised of (a) water, (b) from about 20% to about 40% by weight of sodium laureth-1 sulfate and, (c) from about 25% to about 50% by weight of a $C_{8-16}$ alkyl polyglycoside and a $C_{12-16}$ alkyl polyglycoside. Another preferred composition is comprised of (a) water, (b) from about 20% to about 40% by weight of the sodium salt of the neutralized protein-fatty acid condensate and, (c) from about 25% to about 50% by weight of a $C_{8-16}$ alkyl polyglycoside. Another preferred composition is comprised of (a) water, (b) from about 20% to about 40% by weight of sodium salt of the neutralized protein-fatty acid condensate and, (c) from about 25% to about 50% by weight of a mixture comprising a $C_{8-16}$ alkyl polyglycoside and a $C_{12-16}$ alkyl polyglycoside. Another preferred composition is comprised of (a) water, (b) from about 20% to about 40% by weight of linear alkyl benzene sulfonate and, (c) from about 25% to about 50% by weight of a $C_{8-16}$ alkyl polyglycoside. Another preferred composition is comprised of (a) water, (b) from about 20% to about 40% by weight of linear alkyl benzene sulfonate and, (c) from about 25% to about 50% by weight of a mixture comprising a $C_{8-16}$ alkyl polyglycoside and a $C_{12-16}$ alkyl polyglycoside.

The following examples are meant to illustrate but not limit the invention.

EXAMPLE 1

Into a 2000 ml, 4-neck flask were placed 190 grams (1.0 mole) of a $C_{12-14}$ fatty alcohol. The flask was immersed in an ice bath to cool the contents and placed under vacuum by means of a water aspirator. When the temperature of the fatty alcohol reached 20° C., 116.5 grams (1.0 mole) of chlorosulfonic acid was added from a dropping funnel having a delivery tube long enough to extend below the fatty alcohol surface. The chlorosulfonic acid was added at such a rate as to maintain a reaction temperature in the 20° C.–35° C. range. After the chlorosulfonic acid had been completed, the reaction mixture was stripped under full vacuum for 30 minutes to yield sauer ester.

About 240 grams of the sauer ester were placed in an addition funnel and were added to 760 grams of a neutralization mix comprised of 55 grams of 50% aqueous NaOH, 200 grams of PLANTAREN™ 2000, 300 grams of PLANTAREN™ 1300, 15 grams of CARBOWAX® 400, 160 grams of water, 10 grams of sodium citrate, and 20 grams of KCl. The sauer ester was added to the neutralization mix with vigorous stirring and at a rate which avoided lump formation. The temperature rose to >45° C. The pH was monitored so that it did not fall to the acid side. In the event that the pH did drop below 7.0, sufficient 50% aqueous NaOH was added to restore the pH to an alkaline value. After all the sauer ester was added and the neutralized sauer ester completely dissolved, a sodium citrate buffer was added to bring the pH to a value of 6.0–7.0. The resulting solution contained 25% by weight of neutralized fatty alcohol sulfonate and 25% total of alkyl polyglycoside (a combination of PLANTAREN™ 1300 & 2000) for a total surfactant solids concentration equal to 50% by weight.

EXAMPLE 2

About 35 grams of protein-fatty acid condensate were placed in an addition funnel and were added to a neutralization mix comprised of 7..9 grams of water, 0.5 grams of CARBOWAX® 400, 6.6 grams of 45% aqueous KOH, and 50 grams of PLANTAREN™ 2000. The protein-fatty acid condensate was added to the neutralization mix with vigorous stirring and at a rate which avoided lump formation. The temperature rose to >45° C. The pH was monitored so that it did not fall to the acid side. In the event that the pH did drop below 7.0, sufficient 50% aqueous NaOH was added to restore the pH to an alkaline value. An additional 0.5 grams of CARBOWAX® 400 was added to clear the final product solution, which is the sodium salt of the neutralized protein-fatty acid condensate, had a Brookfield (LVT, spindle #3, @ 12 rpm) viscosity of 4400 cps at 25° C. and a total solids of 51%. The pH at 10% solids was 7.99.

EXAMPLE 3

About 100 grams of APG® 625 Surfactant having a pH of about 11.4 were placed in a 500 ml round-bottomed, 3-neck flask, equipped with an agitator and addition funnel. About 3.88 grams of linear alkyl benzene sulfonic acid were added from the addition funnel. The final mixture contained about 48% of APG® 625 Surfactant and 4% of the sodium salt of linear alkyl benzene sulfonic acid.

EXAMPLE 4

A reactor was charged with 9.5 parts by weight of water, 7 parts by weight of ethanol, 50 parts by weight of APG® 625 Surfactant, 2 parts by weight of sodium sulfate, 6.5 parts by weight of 50% aqueous sodium hydroxide and stirred until the contents became homogeneous. About 20 parts by weight of the acid form of sodium laureth-1 sulfate (sauer ester) were added dropwise with stirring while maintaining the temperature at 25°–30° C. After all the sauer ester was added, the stirring was continued and the temperature was raised to 40° C. and held there for about one-half hour. The pH was maintained at 6.8–7.5 throughout with additions of citric acid as necessary. The product had a total active surfactant content of 50% by weight and was determined to contain 24.6% anionic and had a Brookfield viscosity of 6500–6800 cps at 25° C. (spindle #3 at 12 rpm).

EXAMPLE 5

A reactor was charged with 8.2 parts by weight of water, 6.8 parts by weight of ethanol, 49.2 parts by weight of APG® 625 Surfactant, 2 parts by weight of sodium sulfate, 9.2 parts by weight of 30% aqueous ammonium hydroxide and stirred until the contents became homogeneous. About 24.6 parts by weight of the acid form of sodium laureth-1 sulfate (sauer ester) were added dropwise with stirring while maintaining the temperature at 25°–30° C. After all the sauer ester was added, the stirring was continued and the temperature was raised to 40° C. and held there for about one-half hour. The pH was maintained at 6.8–7.5 throughout with additions of citric acid as necessary. The product had a total active surfactive content of 50% by weight and was determined to contain 23.7% anionic and had a Brookfield viscosity of 700 cps at 25° C. (spindle #2 at 12 rpm).

What is claimed is:

1. A process for making a concentrated surfactant solution which comprises adding the acid form of a neutralizable surfactant to an aqueous composition comprised of a base and a compound of the formula I $$R_1O(Z)_a \qquad I$$

wherein $R_1$ is a monovalent organic radical having from about 6 to about 30 carbon atoms; Z is saccharide residue having 5 or 6 carbon atoms; a is a number having a value from 1 to about 6; wherein the concentration of said base in said aqueous solution is such that the pH of the final surfactant solution has a value of from about 6 to about 8 and wherein the neutralizable surfactant is added in amount such that from about 25% to about 40% by weight of the neutralized surfactant is present in the concentrated surfactant solution and the compound of formula I is present in said aqueous composition in amount such that from about 25% to about 50% by weight thereof is present in the concentrated surfactant solution.

2. The process of claim 1 wherein said compound of formula I is a $C_{8-10}$ alkyl polyglycoside, a $C_{8-16}$ alkyl polyglycoside, or a $C_{12-16}$ alkyl polyglycoside.

3. The process of claim 1 wherein said neutralizable surfactant is the acid form of an alkyl isethionate, an alkyl sarcosinate, a sulfosuccinate, an alkyl ether sulfate, an alkyl taurate, an olefin sulfonate, an alkyl aryl sulfonate, or a protein condensate which is the reaction product of a hydrolyzed protein and a fatty acid chloride.

4. The process of claim 3 wherein said protein condensate is the reaction product of a hydrolyzed collagen having a molecular weight of 500 Daltons and coco fatty acid chloride.

5. The process of claim 1 wherein said base is sodium hydroxide.

6. A process for making a concentrated surfactant solution which comprises adding the reaction product of a $C_{12-14}$ fatty alcohol and chlorosulfonic acid to an aqueous composition comprised of a base and an alkyl polyglycoside selected from the group consisting of a $C_{8-10}$ alkyl polyglycoside, a $C_{8-16}$ alkyl polyglycoside, and a $C_{12-16}$ alkyl polyglycoside wherein the concentration of said base in said aqueous composition is such that the pH of the final surfactant solution has a value of from about 6 to about 8 to form a neutralized reaction product and wherein said reaction product is added in amount such that from about 25% to about 40% by weight of the neutralized reaction product is present in the concentrated surfactant solution and said alkyl polyglycoside is present in said aqueous composition in amount such that from about 25% to about 50% by weight thereof is present in the concentrated surfactant solution.

7. The process of claim 6 wherein said base is sodium hydroxide.

8. A process for making a concentrated surfactant solution which comprises adding the reaction product of a hydrolyzed protein and a fatty acid chloride to an aqueous composition comprised of a base and a compound of the formula I $$R_1O(Z)_a \quad \text{I}$$

wherein $R_1$ is a monovalent organic radical having from about 6 to about 30 carbon atoms; Z is saccharide residue having 5 or 6 carbon atoms; a is a number having a value from 1 to about 6; wherein the concentration of said base in said aqueous composition is such that the pH of the final surfactant solution has a value of from about 6 to about 8 to form a neutralized reaction product and wherein said reaction product is added in amount such that from about 25% to about 40% by weight of the neutralized reaction product is present in the concentrated surfactant solution and the compound of formula I is present in said aqueous composition in amount such that from about 25% to about 50% by weight thereof is present in the concentrated surfactant solution.

9. The process of claim 8 wherein said compound of formula I is a $C_{8-10}$ alkyl polyglycoside, a $C_{8-16}$ alkyl polyglycoside, or a $C_{12-16}$ alkyl polyglycoside.

10. The process of claim 8 wherein said hydrolyzed protein is hydrolyzed collagen having a molecular weight of 500 Daltons.

11. The process of claim 8 wherein said fatty acid chloride is coco fatty acid chloride.

12. A composition comprising: (a) water, (b) from about 20% to about 40% by weight of the sodium salt of an anionic surfactant selected from the group consisting of: an alkyl isethionate, an alkyl sarcosinate, a sulfosuccinate, an alkyl ether sulfate, an alkyl taurate, an olefin sulfonate, an alkyl aryl sulfonate, a protein condensate which is the reaction product of a hydrolyzed protein and a fatty acid chloride, and a mixture thereof, (c) from about 25% to about 50% by weight of a compound of the formula I $$R_1O(Z)_a \quad \text{I}$$

wherein $R_1$ is a monovalent organic radical having from about 6 to about 30 carbon atoms; Z is a saccharide residue having 5 or 6 carbon atoms; a is a number having a value from 1 to about 6 wherein the composition is in the form of a concentrated solution.

13. The composition of claim 12 wherein said anionic surfactant is an alkyl ether sulfate.

14. The composition of claim 13 wherein said alkyl ether sulfate is sodium laureth-1 sulfate.

15. The composition of claim 12 wherein said anionic surfactant is an alkyl aryl sulfonate.

16. The composition of claim 15 wherein said alkyl aryl sulfonate is linear alkyl benzene sulfonate.

17. The composition of claim 12 wherein said compound of formula I is a $C_{8-16}$ alkyl polyglycoside.

18. The composition of claim 12 wherein said compound of formula I is a $C_{12-16}$ alkyl polyglycoside.

19. The composition of claim 12 wherein said compound of formula I is a $C_{12-16}$ alkyl polyglycoside having an average degree of polymerization of 1.4.

20. A composition consisting essentially of: (a) water, (b) from about 25% to about 40% by weight of the sodium salt of a neutralized protein-fatty acid condensate and, (c) from about 25% to about 50% by weight of a $C_{8-16}$ alkyl polyglycoside, wherein the composition is in the form of a concentrated solution.

21. A composition consisting essentially of: (a) water, (b) from about 25% to about 40% by weight of the sodium salt of a neutralized protein-fatty acid condensate and, (c) from about 25% to about 50% by weight of a $C_{12-16}$ alkyl polyglycoside, wherein the composition is in the form of a concentrated solution.

22. A composition consisting essentially of: (a) water, (b) from about 25% to about 40% by weight of the sodium salt of a neutralized protein-fatty acid condensate and, (c) from about 25% to about 50% by weight of a $C_{12-16}$ alkyl polyglycoside having an average degree of polymerization of 1.4, wherein the composition is in the form of a concentrated solution.

23. A composition consisting essentially of: (a) water, (b) from about 25% to about 40% by weight of sodium salt of a neutralized protein-fatty acid condensate and, (c) from about 25% to about 50% by weight of a mixture comprising a $C_{8-16}$ alkyl polyglycoside and a $C_{12-16}$ alkyl polyglycoside, wherein the composition is in the form of a concentrated solution.

24. A composition consisting essentially of: (a) water, (b) from about 25% to about 40% by weight of an alkyl aryl sulfonate and, (c) from about 25% to about 50% by weight of a mixture comprising a $C_{8-16}$ alkyl polyglycoside and a $C_{12-16}$ alkyl polyglycoside, wherein the composition is in the form of a concentrated solution.

25. A composition consisting essentially of: (a) water, (b) from about 25% to about 40% by weight of an alkyl aryl sulfonate and, (c) from about 25% to about 50% by weight of a $C_{8-16}$ alkyl polyglycoside, wherein the composition is in the form of a concentrated solution.

26. A composition consisting essentially of: (a) water, (b) from about 25% to about 40% by weight of an alkyl ether sulfate and, (c) from about 25% to about 50% by weight of a mixture comprising a $C_{8-16}$ alkyl polyglycoside and a $C_{12-16}$ alkyl polyglycoside, wherein the composition is in the form of a concentrated solution.

27. A composition consisting essentially of: (a) water, (b) from about 25% to about 40% by weight of an alkyl ether sulfate and, (c) from about 25% to about 50% by weight of a $C_{8-16}$ alkyl polyglycoside, wherein the composition is in the form of a concentrated solution.

* * * * *